United States Patent
Yeh et al.

(10) Patent No.: US 10,247,658 B2
(45) Date of Patent: Apr. 2, 2019

(54) TEST JIG FOR COATING ADHESION STRENGTH

(71) Applicant: UNIVERSAL GLOBAL TECHNOLOGY (SHANGHAI) CO., LTD., Shanghai (CN)

(72) Inventors: Chih-Kao Yeh, Caotun Township (TW); Xiao-Li Shao, Caotun Township (TW)

(73) Assignee: UNIVERSAL GLOBAL TECHNOLOGY (SHANGHAI) CO., LTD., Shanghai (CN)

( * ) Notice: Subject to any disclaimer, the term of this patent is extended or adjusted under 35 U.S.C. 154(b) by 237 days.

(21) Appl. No.: 15/070,798

(22) Filed: Mar. 15, 2016

(65) Prior Publication Data

US 2017/0122862 A1  May 4, 2017

(30) Foreign Application Priority Data

Oct. 28, 2015  (CN) .......................... 2015 1 0712379

(51) Int. Cl.
*G01N 19/04* (2006.01)
*G01N 35/00* (2006.01)

(52) U.S. Cl.
CPC ......... *G01N 19/04* (2013.01); *G01N 35/0099* (2013.01); *G01N 2203/0091* (2013.01)

(58) Field of Classification Search
CPC .......... G01N 19/04; G01N 11/00; G01N 3/58; G01N 35/0099; G01N 2203/0091; B26F 3/00; C03B 33/023

USPC .......... 73/150, 159, 862.01, 862, 865.6, 866
See application file for complete search history.

(56) References Cited

U.S. PATENT DOCUMENTS

| | | | | |
|---|---|---|---|---|
| 3,747,397 A * | 7/1973 | Sharabash | ........... | G01N 11/00 118/712 |
| 6,766,696 B2 * | 7/2004 | Nishiyama | ........... | G01N 19/04 73/762 |
| 9,207,161 B2 * | 12/2015 | Chang | ................. | G01N 19/04 |
| 9,375,723 B2 * | 6/2016 | Breja | ................... | B02C 18/186 |
| 2016/0068793 A1 * | 3/2016 | Maggiore | .......... | B29C 67/0085 435/289.1 |

FOREIGN PATENT DOCUMENTS

CN          204314203      *    5/2015    ........... G01N 19/04

* cited by examiner

*Primary Examiner* — Lisa M Caputo
*Assistant Examiner* — Nigel H Plumb
(74) *Attorney, Agent, or Firm* — Muncy, Geissler, Olds & Lowe, P.C.

(57) ABSTRACT

A test jig for coating adhesion strength includes a base, a sample carrier, a first displacement mechanism and a second displacement mechanism mounted on the base, and a cutting knife holder equipped with two differently oriented cutting knives that is mounted between the second displacement mechanism and the sample carrier. The sample carrier, the first displacement mechanism and the second displacement mechanism can be driven to move such that the cutting knives can exert a constant pressure to cut the sample on the sample carrier.

9 Claims, 6 Drawing Sheets

TEST JIG FOR COATING ADHESION STRENGTH

BACKGROUND OF THE INVENTION

1. Field of the Invention

The present invention relates to coating adhesion strength test technology, and more particularly, to a coating adhesion strength test jig that can automatically and accurately test the coating adhesion strength of a sample.

2. Description of the Related Art

Conventionally, the test method for evaluating the coating adhesion strength is described as follows. Using a specific cutting knife to cut a grid pattern on the surface of the coating, adhering an adhesive tape to the grid pattern and removing the adhesive tape from the grid pattern. Then, evaluating the coating adhesion strength by checking the peeling status. Normally, coating adhesion strength can be classified into the following six grades:

|  | Class. | | | | |
|---|---|---|---|---|---|
| 5 | 4 | 3 | 2 | 1 | 0 |
| Peeling status No peeling | Peel-off area <5% | Peel-off area within 5-15% | Peel-off area within 15-35% | Peel-off area within 35-65% | Peel-off area >65% |

Conventionally, the procedure of cutting a grid pattern on the coating relies on labors. This test method usually has the following drawbacks: (1) It is difficult to precisely control the cutting angle, the cutting pressure and the cutting velocity of the cutting knife in cutting the surface of the coating, and thus, the cutting result is usually lack of consistency, lowering the reliability of the test result;(2) This manual cutting procedure is not applicable to a sample with its surface area smaller than 1 cm², or a sample having an uneven surface;(3) The labor may be cut accidentally. Therefore, there is a demand for a test jig for coating adhesion strength evaluation that eliminates the aforesaid drawbacks.

SUMMARY OF THE INVENTION

The present invention has been accomplished under the circumstances in view. It is an objective of the present invention to provide a test jig for coating adhesion strength, which can accurately measure the adhesion strength of the coating on the test sample.

It is another objective of the present invention to provide a test jig, which can implement the test method automatically.

To achieve these and other objects of the present invention, a test jig for coating adhesion strength is provide to comprises a base, a sample carrier, a first displacement mechanism, a second displacement mechanism, a cutting knife holder and two cutting knives. The sample carrier is mounted on the base and drivable to move along a first direction. The first displacement mechanism is mounted on the base above the sample carrier, comprising a first positioning member that is drivable to move in a second direction. The second displacement mechanism is mounted at the first positioning member, comprising a second positioning member that is drivable to move in a third direction. The cutting knife holder is mounted on the second positioning member, comprising a first face and a second face that hold the two cutting knives respectively.

Thus, the test jig can automatically control the movement of the sample carrier and the cutting knife to further precisely control the cutting velocity and cutting pressure of the cutting knives, making each cut substantially the same and enhancing the reliability of the test result.

Preferably, the test jig may have a locating plate which is fixedly mounted at the second positioning member so that the cutting knife holder can be movably mounted at the second positioning member by the locating plate. Preferably, a load cell is provided and connected with two opposite ends thereof to the locating plate and the cutting knife holder respectively. Thus, the cutting pressures detected by the load cell can be fed back to control the position of the second positioning member such that the cutting knives can cut the coating under the condition of the same pressure, overcoming the problem of poor surface flatness of the sample.

Other and further benefits, advantages and features of the present invention will be understood by reference to the following specification in conjunction with the accompanying drawings, in which like reference characters denote like elements of structure.

DETAILED DESCRIPTION OF THE INVENTION

Figure 1:
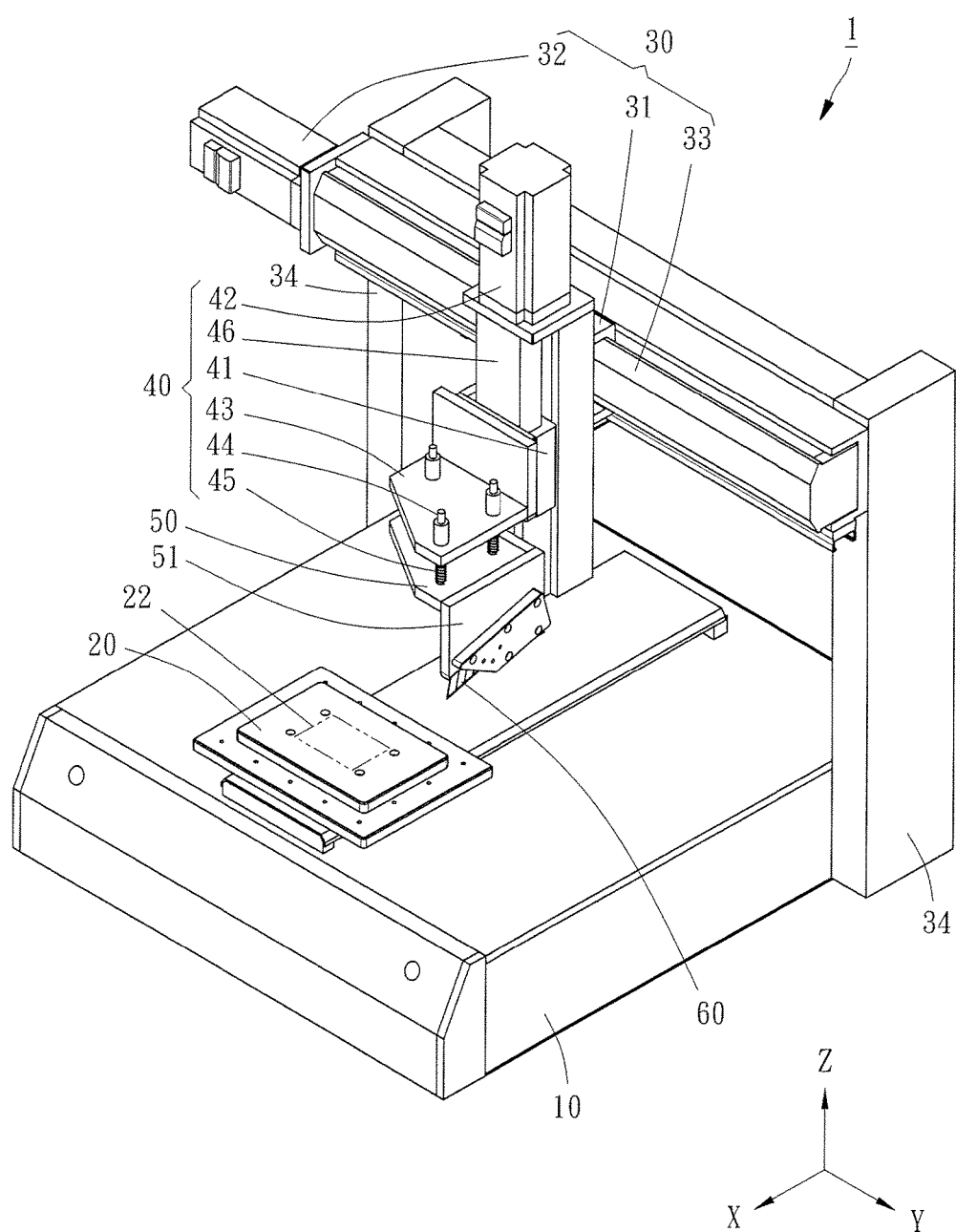
FIG. 1 is an oblique top elevational view of a test jig for testing coating adhesive strength in accordance with the present invention.
Figure 2:
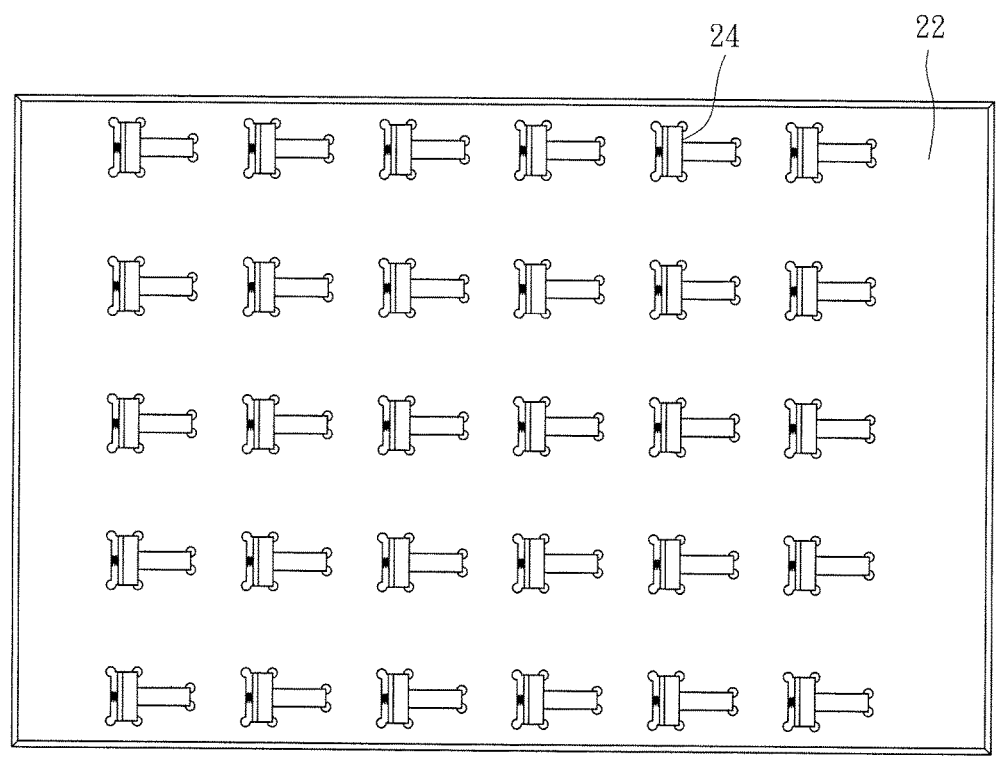
FIG. 2 is a schematic enlarged view of the sample loading zone of the sample carrier in accordance with the present invention.
Figure 3:
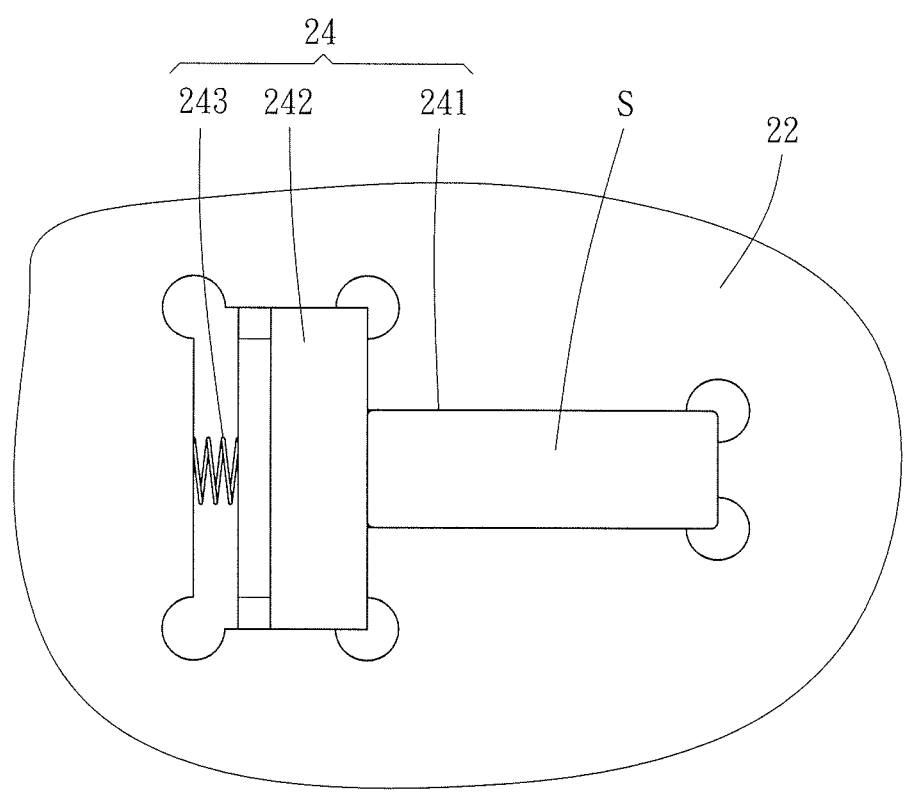
FIG. 3 is a top view of one sample locating unit shown in FIG. 2.

Referring to FIGS. 1-3, to facilitate explanation of an embodiment of the present invention, a first direction, a second direction and a third direction hereinafter described are respectively referred to X-axis direction, Y-axis direction and Z-axis direction of a Cartesian coordinate system, wherein the first direction, the second direction and the third direction are respectively disposed perpendicular to one another, however, the first, second and third directions described in the present preferred embodiment are not limited to the aforesaid Cartesian coordinate system.

The coating adhesion strength test jig 1 comprises a base 10, a sample carrier 20, a first displacement mechanism 30, a second displacement mechanism 40, a cutting knife holder 50, two cutting knives 60 and a controller (not shown). The structure of these components parts and their relationship are described hereinafter.

Referring first to FIG. 1, the sample carrier 20 is mounted on the base 10. The sample carrier 20 can be driven by a first motor (not shown; disposed below the sample carrier 20) to move along the X-axis direction. In this embodiment, the sample carrier 20 and the base 10 jointly constitute of a linear guideway. Further, the sample carrier 20 comprises a sample loading zone 22 located at a center of the sample carrier 20 and used for loading samples S.

Please referring to FIG. 2 and FIG. 3 wherein FIG. 2 is a schematic enlarged view of the sample loading zone 22. As illustrated, the sample loading zone 22 defines thirty sample locating units 24 that are arranged in a 6×5 array, wherein each sample locating unit 24 is for locating one respective sample S. FIG. 3 is a top view of the sample locating unit 24. As illustrated, the sample locating unit 24 comprises a locating groove 241, a pressure member 242 and a spring member 243. The sample S, the pressure member 242 and the spring member 243 are accommodated in the locating groove 241. The sample S has three sides thereof abutted against an inside wall of the locating groove 241 and the other side thereof abutted against the pressure member 242. The spring member 243 has two opposite ends thereof respectively abutted against the inside wall of the locating groove 241 and the pressure member 242, such that the sample S can be firmly located in the locating groove 241 by the pressure member 242.

Figure 4:
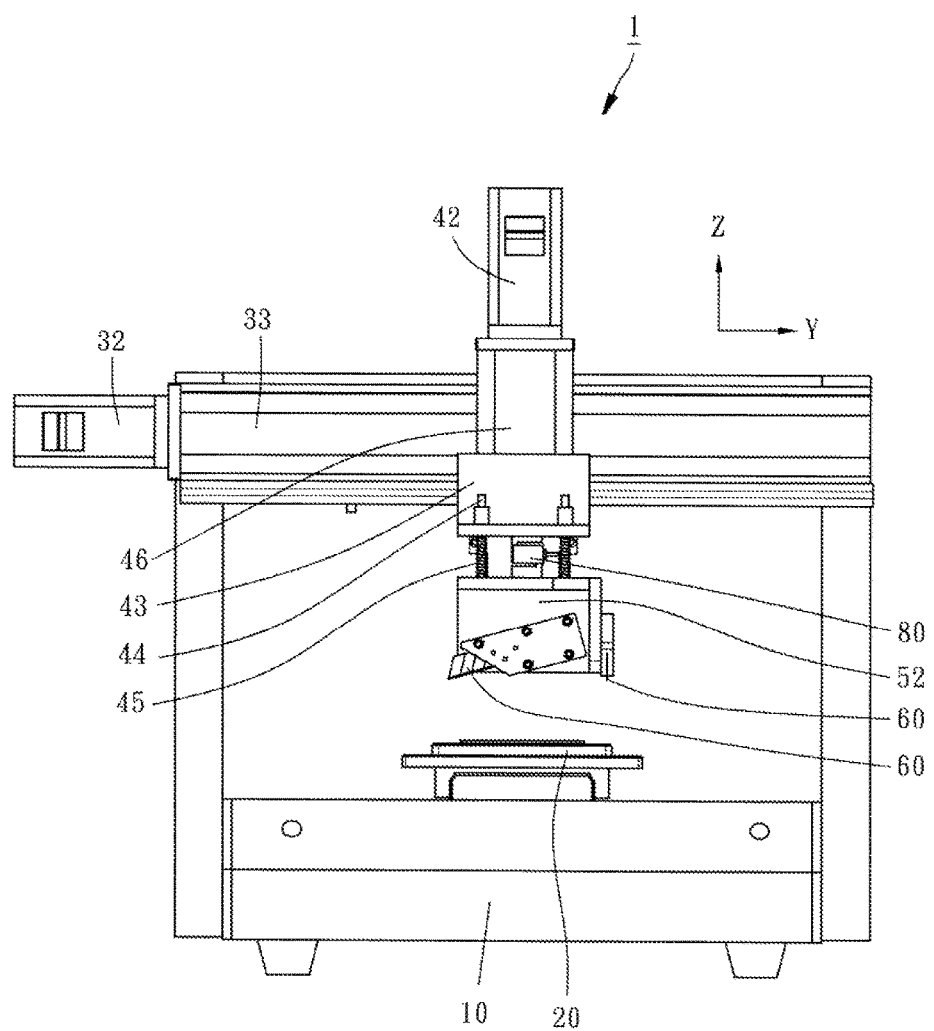
FIG. 4 is a side view of the test jig in accordance with the present invention.

Referring to FIG. 4 and FIG. 1, the first displacement mechanism 30 is mounted on the base 10. The first displacement mechanism 30 comprises a first positioning member 31, a second motor 32 and a first sliding rail 33. The first sliding rail 33 is horizontally supported above the base 10 and the sample carrier 20 by two uprights 34 and extended in the Y-axis direction. The first positioning member 31 is a sliding block slidably mounted on the first sliding rail 33. The second motor 32 is mounted at one side of the first sliding rail 33 and adapted for driving the first positioning member 31 to move in the Y-axis direction.

Figure 5:
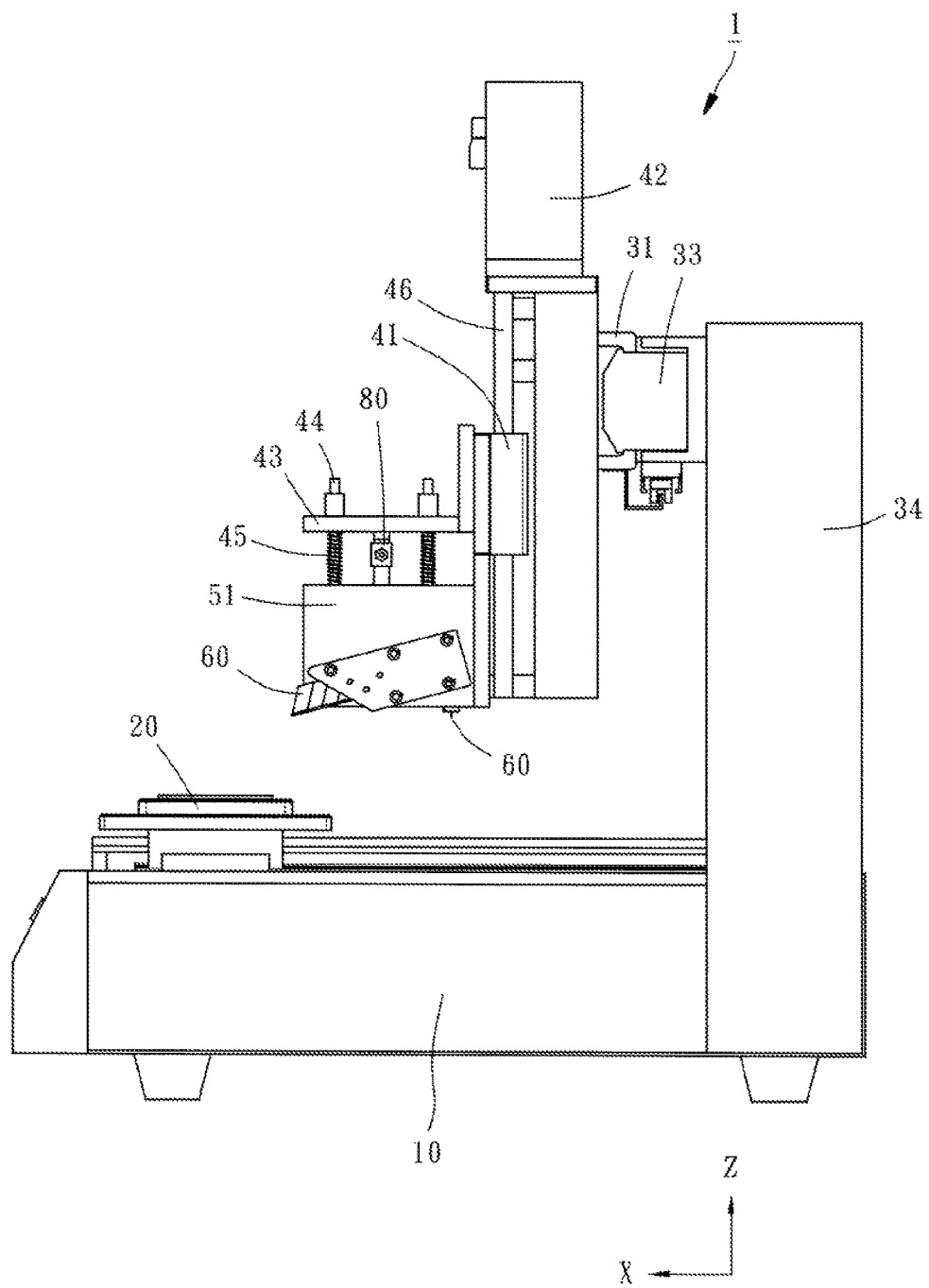
FIG. 5 is another side view of the test jig in accordance with the present invention.

Referring to FIG. 5 and FIG. 1, the second displacement mechanism 40 is mounted at the first positioning member 31 of the first displacement mechanism 30 The second displacement mechanism 40 comprises a second positioning member 41, a third motor 42, and a second sliding rail 46 extended in the Z-axis direction. The second positioning member 41 is a sliding block slidably mounted on the second sliding rail 46, and the second positioning member 41 can be driven by the third motor 42 to move along the Z-axis direction. In this exemplary embodiment, the first displacement mechanism 30 further optionally comprises a locating plate 43, three connection rods 44 and three compression springs 45. The locating plate 43 is fixedly mounted at the second positioning member 41. The connection rods 44 each have one end fixedly connected to the locating plate 43 and an opposite end movably connected with the cutting knife holder 50. The compression springs 45 are respectively coaxially sleeved onto the connection rods 44 and respectively abutted against the locating plate 43 and the cutting knife holder 50 for lessening the vibration of the cutting knife holder 50.

It is to be noted that the first motor, the second motor 32 and the third motor 42 in this exemplary embodiment are step motors. However, other kinds of driving devices can be used. Further, the amount of the connection rods 44 and the compression springs 45 are not limited to three.

The cutting knife holder 50 is mounted at the second positioning member 41 by means of the locating plate 43. The cutting knife holder 50 comprises a first face 51 substantially in parallel to the X-axis direction (see FIG. 5), and a second face 52 substantially in parallel to the Y-axis direction (see FIG. 4). Further, a load cell 80 is set between the cutting knife holder 50 and the locating plate 43. As illustrated in FIG. 2, the load cell 80 is adapted for measuring the pressures that are applied by the cutting knives 60 to the coating, and therefore, the two opposite ends of the load cell 80 can be respectively connected to the locating plate 43 and the cutting knife holder 50.

Figure 6:
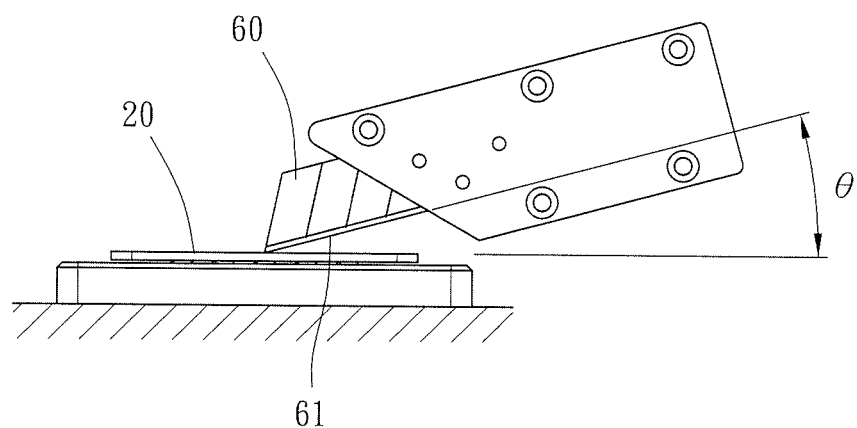
FIG. 6 is a schematic drawing illustrating the contained angle between the cutting knife and the coating.

The two cutting knives 60 are respectively mounted on the first face 51 and second face 52 of the cutting knife holder 50, and thus, the cutting knives 60 can cut the coating in the X-axis direction and the Y-axis direction respectively. Further, the contained angle between the cutting edge 61 of the cutting knife 60 and the sample carrier 20 is adjustable. In this embodiment, the contained angle θ between the cutting edge 61 and the sample carrier 20 is adjusted to 15 degrees angle. (see FIG. 6).

The controller (not shown) is adapted for driving the first motor, the second motor 32 and the third motor 42, and the controller can synchronously control each motor's moving steps and velocity to further control the position, cutting velocity and cutting pressure of the cutting knives 60 and the position and moving speed of the sample carrier 20. In this embodiment, the controller is mounted in the base 10, and edited motor control commands can be burned into the controller to control the operation of the motors by a programmer. Further, in other situation, the controller can be a host computer, which can drive and control each motor by means of implementation of a predetermined software program.

The structure of each component of the test jig 1 and their relative relationship are detailed. The application of the test jig 1 is disclosed hereinafter.

When an operator wants to perform the test method, first locate the sample S in the sample loading zone 22. Then the controller drives the first motor, the second motor 32 and the third motor 42 to move the cutting knives 60 toward the sample S and make the cutting knives 60 cut the coating of the sample S. At this time, the controller measures the cutting pressure of the cutting knives 60 via the load cell 80 and controls the cutting knives 60 to cut a plurality of cutting lines which are aligned parallel to the X-axis or the Y-axis under the condition of a constant interval and equal pressure subject to the specifications of the test method, therefore forming the grip pattern.

It is to be noted that when one of the cutting knives 60 is driven to cut the sample S, the operator may adjust the position or the contained angle of the other cutting knife 60 that is not in operation, preventing this non-operative cutting knife 60 from touching the sample carrier 20 accidentally.

In the present embodiment, the two cutting knives 60 are mounted on the first face 51 and second face 52 of the cutting knife holder 50 and oriented in different directions beforehand, therefore, it is not necessary to rotate the cutting knife holder 50 to cut the coating or to dismount the sample S during the test procedures, simplifying the test procedures and saving test time.

In the present embodiment, driving each motor to automatically and precisely control the contained angle, the cutting velocity, and the cutting pressure of each cutting, it enhances the reliability of the test result and avoids the operator from accidental injuries. Further, due to high stepper motor control precision, the cutting knives 60 can be controlled to cut a small area of the coating, and therefore, the test jig 1 of the present invention is practical for testing the coating adhesion strength of a sample S that has a small surface area.

On the other hand, the invention can also be used to test samples S that have an uneven surface. More specifically, subject to the pressure instantly detected by the load cell 80, the controller can real-time detect the cutting pressure via load cell 80 such that the cutting knives 60 can cut the grid pattern under the condition of maintaining equal cutting pressure at different locations of the uneven surface.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A coating adhesion strength test jig, comprising:
   a base;
   a sample carrier mounted on said base and drivable to move along a first direction;
   a first displacement mechanism mounted on said base above said sample carrier, said first displacement mechanism comprising a first positioning member drivable to move along a second direction;
   a second displacement mechanism mounted to said first positioning member, said second displacement mechanism comprising a second positioning member drivable to move along a third direction;
   a cutting knife holder mounted to said second positioning member, said cutting knife holder comprising a first face and a second face; and
   two cutting knives respectively mounted on said first face and said second face;
   wherein said test jig further comprises a load cell mounted between said second positioning member and said cutting knife holder;
   wherein said second displacement mechanism further comprises a locating plate fixedly mounted to said second positioning member; said cutting knife holder is movably mounted to said second positioning member by said locating plate, and said load cell has two opposite ends thereof respectively connected to said locating plate and said cutting knife holder.

2. The test jig as claimed in claim 1, wherein said second displacement mechanism further comprises at least one connection rod; said at least one connection rod has one end thereof fixedly connected to said locating plate and an opposite end thereof movably connected with said cutting knife holder.

3. The test jig as claimed in claim 2, wherein said second displacement mechanism further comprises at least one compression spring respectively sleeved onto said at least one connection rod; each said compression spring has two opposite ends thereof respectively abutted against said locating plate and said cutting knife holder.

4. The test jig as claimed in claim 1, wherein each said cutting knife comprises a cutting edge that defines with said sample carrier a contained angle of 15 degrees angle.

5. The test jig as claimed in claim 1, further comprises three motors adapted for driving said sample carrier, said first positioning member and said second positioning member respectively, and said motors are stepper motors.

6. The test jig as claimed in claim 1, wherein said first direction, said second direction and said third direction form a Cartesian coordinate system; said first face and said second face of said cutting knife holder are substantially disposed in parallel to said first direction and said second direction respectively.

7. The test jig as claimed in any of claim 1, wherein said first displacement mechanism comprises a first sliding rail; said second displacement mechanism comprises a second sliding rail; said first positioning member and said second positioning member are sliding blocks respectively slidably mounted on said first sliding rail and said second sliding rail.

8. The test jig as claimed in claim 7, further comprises a controller adapted for controlling the cutting velocity and cutting pressure of each said cutting knife.

9. The test jig as claimed in any of claim 1, wherein said sample carrier comprises at least one sample locating unit; each said sample locating unit comprises a locating groove, a pressure member and a spring member; said pressure member and said spring member are accommodated in said locating groove, said spring member has two opposite ends thereof respectively abutted against an inside wall of said locating groove and said pressure member.

* * * * *